Sept. 7, 1954 P. E. SHEPP Plant Pat. 1,300
CAMELLIA PLANT
Filed June 29, 1953
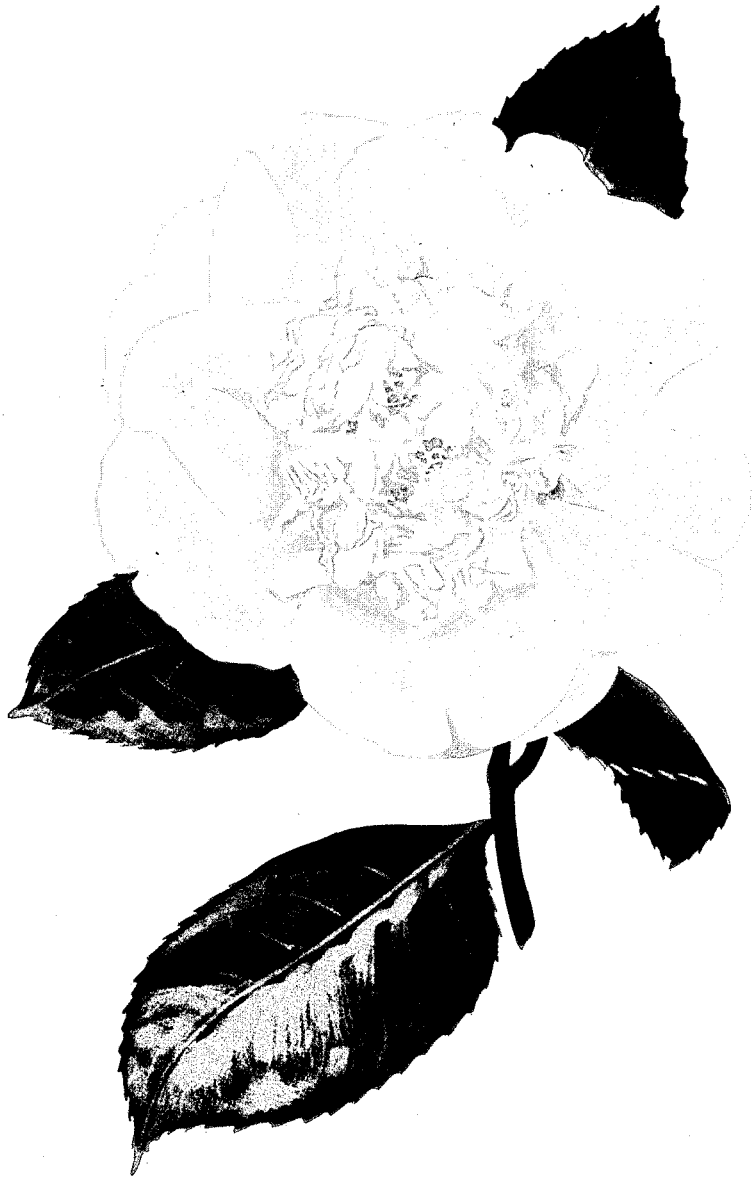
INVENTOR.
PAUL E. SHEPP
BY James B. Chutter
ATTORNEY Patented Sept. 7, 1954

Plant Pat. 1,300

UNITED STATES PATENT OFFICE 1,300

CAMELLIA PLANT

Paul E. Shepp, Pasadena, Calif.

Application June 29, 1953, Serial No. 364,977

1 Claim. (Cl. 47—60)

The present invention relates to a new and distinct variety of camellia plant comprising a white sport or mutation discovered by me on a Camellia Japonica C. M. Wilson, growing on my property in Pasadena, California; the C. M. Wilson in turn being a sport or mutation of Camellia Japonica Chandleri Elegance. To the best of my knowledge neither of these varieties is patented.

The new variety is particularly characterized by a predominately white color, distinguishing it from its parent and from the Chandleri Elegance family. The new variety possesses all the advantages of the Chandleri Elegance family with respect to size, durability, profuse blooming and easy propagation and is, in these respects, an improvement over other white camellias.

This new variety of camellia was reproduced asexually in Pasadena, California, by both cuttings and grafting, and has proven to be easily reproducible by either of these methods. Such reproduction shows that the characteristics of the plant, as herein set forth, come true to form and are fixed and transmitted through such propagation.

In the accompanying drawings are shown specimens of the new variety, showing both the foliage and bloom.

The following is a detailed description of the new variety, with color terminology in accordance with the Horticultural Color Chart issued by the British Color Council in collaboration with the Royal Horticultural Society.

The bud, flower (excepting color), foliage and growth habits are identical to that of C. M. Wilson or Chandleri Elegance.

Bloom:

*Size.*—4½" to 5¼" in diameter.

*Borne.*—Usually two on extremities of each stem.

*Form.*—Anemone.

*Petalage.*—Obovate petal showing notched apex and slightly tapered base; three overlying rows totaling 15 to 25 radially extending petals; profuse cluster of petaloids in center (approximately 100 to 150), with golden yellow stamens intermixed.

Color: Petals—white with triangular region of Camellia Rose at base of some of petals. Camellia Rose characterized as 622/3 in above cited color reference. This color fades in two or three days after blooming. Reverse side of petals same as obverse side.

*Petaloids.*—White.

*Stamens.*—Golden yellow.

Fragrance: None.

Lasting quality: Excellent.

Season: December to April.

I claim:

A new and distinct variety of camellia japonica plant characterized as to novelty by the combination of qualities of its parent Camellia Japonica C. M. Wilson, and by the unmottled white color of the flowers substantially as shown and described.

No references cited.